US011590251B2

(12) United States Patent
Furudate et al.

(10) Patent No.: US 11,590,251 B2
(45) Date of Patent: Feb. 28, 2023

(54) DEODORIZING/ANTIBACTERIAL/ANTIFUNGAL AGENT, METHOD OF PREPARATION THEREOF, AND MEMBER HAVING DEODORIZING/ANTIBACTERIAL/ANTIFUNGAL AGENT ON SURFACE

(71) Applicant: Shin-Etsu Chemical Co., Ltd., Tokyo (JP)

(72) Inventors: Manabu Furudate, Kamisu (JP); Tomohiro Inoue, Kamisu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 30 days.

(21) Appl. No.: 16/144,336

(22) Filed: Sep. 27, 2018

(65) Prior Publication Data

US 2019/0099510 A1    Apr. 4, 2019

(30) Foreign Application Priority Data

Sep. 29, 2017  (JP) .............................. JP2017-190160

(51) Int. Cl.
| A61L 2/238 | (2006.01) |
| A61L 9/014 | (2006.01) |
| A01N 59/16 | (2006.01) |
| C01G 5/00 | (2006.01) |
| C01G 23/00 | (2006.01) |
| C01G 23/047 | (2006.01) |
| B82Y 30/00 | (2011.01) |

(52) U.S. Cl.
CPC .............. *A61L 2/238* (2013.01); *A01N 59/16* (2013.01); *A61L 9/014* (2013.01); *C01G 5/006* (2013.01); *C01G 23/002* (2013.01); *C01G 23/047* (2013.01); *A61L 2202/25* (2013.01); *B82Y 30/00* (2013.01)

(58) Field of Classification Search
CPC ......... A01N 59/16; A01N 59/20; A61L 2/238; B82Y 30/00; C01G 23/002; C01G 23/047; C01G 5/006
USPC .................. 442/123; 427/217; 977/773, 775, 977/777–779, 783; 424/404, 405
See application file for complete search history.

(56) References Cited

U.S. PATENT DOCUMENTS

| 6,121,298 | A | * | 9/2000 | Sakamoto | ............ | C08K 5/0058 |
| | | | | | | 514/359 |
| 6,313,064 | B1 | * | 11/2001 | Miyafuji | ................ | A01N 59/16 |
| | | | | | | 502/331 |
| 8,486,433 | B2 | | 7/2013 | Tanaka et al. | | |
| 8,546,355 | B2 | | 10/2013 | Uchiyama et al. | | |
| 2013/0177504 | A1 | * | 7/2013 | Macoviak | ............ | A61K 33/242 |
| | | | | | | 424/10.3 |
| 2014/0205546 | A1 | | 7/2014 | Macoviak | | |

FOREIGN PATENT DOCUMENTS

| CN | 101745271 A | 6/2010 | | |
| CN | 101745271 B | * 9/2011 | | |
| EP | 0937398 A1 | * 8/1999 | ............ | A01N 25/08 |
| JP | 2686638 B2 | 12/1997 | | |
| JP | 11-228306 A | 8/1999 | | |
| JP | 2001-37861 A | 2/2001 | | |
| JP | 2001-70423 A | 3/2001 | | |
| JP | 2001-178806 A | 7/2001 | | |
| JP | 2002-345933 A | 12/2002 | | |
| JP | 2003-113392 A | 4/2003 | | |
| JP | 2003-533588 A | 11/2003 | | |
| JP | 2005-318999 A | 11/2005 | | |
| JP | 2008-105920 A | 5/2008 | | |
| JP | 2013-126654 A | 6/2013 | | |
| WO | 2013/073695 A1 | 5/2013 | | |
| WO | WO-2014141812 A1 | * 9/2014 | ............... | C09D 5/14 |
| WO | 2016/152487 A1 | 9/2016 | | |

OTHER PUBLICATIONS

Office Action dated Mar. 31, 2020, issued in counterpart JP Application No. 2017-190160, with English translation (8 pages).
Office Action dated Dec. 8, 2020, issued in counterpart JP Application No. 2017-190160, with English translation (6 pages).
Office Action dated Mar. 22, 2021, issued in counterpart CN application No. 201811134628.5, with English translation. (14 pages).
Office Action dated Aug. 25, 2021, issued in counterpart CN application No. 201811134628.5, with English translation. (17 pages).

* cited by examiner

*Primary Examiner* — Matthew D Matzek
(74) *Attorney, Agent, or Firm* — WHDA, LLP

(57) ABSTRACT

A deodorizing/antibacterial/antifungal agent containing two kinds of fine particles, (i) titanium oxide fine particles and (ii) alloy fine particles containing an antibacterial/antifungal metal, gives a thin film of high transparency which has deodorizing properties and also exhibits antibacterial/antifungal properties.

10 Claims, No Drawings

DEODORIZING/ANTIBACTERIAL/ANTIFUNGAL AGENT, METHOD OF PREPARATION THEREOF, AND MEMBER HAVING DEODORIZING/ANTIBACTERIAL/ANTIFUNGAL AGENT ON SURFACE

CROSS-REFERENCE TO RELATED APPLICATION

This non-provisional application claims priority under 35 U.S.C. § 119(a) on Patent Application No. 2017-190160 filed in Japan on Sep. 29, 2017, the entire contents of which are hereby incorporated by reference.

TECHNICAL FIELD

This invention relates to a deodorizing/antibacterial/antifungal agent, a method for preparing the same, and a member having the deodorizing/antibacterial/antifungal agent on a surface thereof. More particularly, the invention relates to a deodorizing/antibacterial/antifungal agent that gives a highly transparent thin film which has deodorizing properties and also exhibits antibacterial/antifungal properties, a method for preparing such an agent, and a member having the deodorizing/antibacterial/antifungal agent on a surface thereof.

BACKGROUND ART

Consumers today expect their living space to be safe, secure, healthy and pleasant. There is a great deal of interest both in minimizing unpleasant odors intimately connected with the living environment, such as harmful volatile organic compounds (VOCs) that are released by products used in everyday life and by buildings, the smell of sweat, body odor in older people, the smell of cigarettes and the smell of garbage, and also in preventing microbial contamination by bacteria, mildew and the like.

Methods for removing bad smells with deodorizers include chemical deodorization, physical deodorization, sensory deodorization and biological deodorization, and are selectively used according to the intended purpose. Chemical deodorization renders an odor-causing substance odorless by causing it to chemically react with a deodorizing ingredient, and thus enables highly selective deodorization targeted at specific odor-causing substances. Physical deodorization, which removes odor-causing substances from air by physical adsorption, makes it relatively easy to carry out the deodorization of a plurality of odor-causing substances at the same time with a single deodorizer. Substances such as activated carbon, zeolites, silica gel, alumina, titania and cyclodextrin are used as the adsorbent. Sensory deodorization, which is a method of deodorization that eliminates the undesirable sensation by masking or pairing the offending odor with aromatic ingredients, differs from other methods of deodorization in that the odor-causing substance is not removed from the space and therefore cannot be regarded as effective from a health standpoint. Biological deodorization is a method that suppresses odor formation itself by suppressing bacterial growth.

Spray-type deodorizers which use one or a combination of several of these methods of deodorization are known, although such deodorizers have an inadequate deodorizing ability and persistence.

Given the characteristics of the various methods of deodorization, physical deodorization is preferred for removing a variety of unpleasant odors that are present in living spaces. Depending on the conditions and the place, combining other methods of deodorization with physical deodorization can be even more preferable.

For example, the smell of sweat arises when bacteria proliferate due to the presence of sweat and these bacteria break down sebum and other substances that have mingled with the sweat. Toilet smell contains as a main ingredient the ammonia that forms when bacteria multiply due to the presence of urine on and around the toilet and these bacteria break down the urine. Hence, suppressing the growth of these bacterial is effective for suppressing the formation of bad odors. Combining biological deodorization with physical deodorization thus appears to be more effective because, along with removing bad odors, the formation of such odors itself can be suppressed.

Products obtained by adding an antibacterial agent to an adsorbent hitherto used in physical deodorization have been commercialized as antibacterial/deodorizing agents, but most lack a sufficient deodorizing/antibacterial ability and few if any exhibit an antifungal activity. Moreover, because most such adsorbents are granular or powdery and therefore cannot be sprayed or misted in air, it takes time for bad odors to come into contact with the adsorbent and be adsorbed, making it difficult to obtain a rapid effect. In addition, it has been difficult to impart deodorizing/antibacterial/antifungal properties by depositing such a product on, for example, construction materials for building interiors and exteriors, furniture, textile products such as clothing and curtains, and electrical appliances while retaining the decorative qualities of these items.

Antibacterial/antifungal agents can be broadly divided into organic agents and inorganic agents. The synthetic organic antibacterial/antifungal agents that have hitherto been commonly used are inexpensive and effective even in small amounts. Yet, they often exhibit efficacy only against certain microorganisms (the antimicrobial spectrum is narrow); the difference in their effects on, for example, Gram-negative bacteria, Gram-positive bacteria and molds is sometimes considerable. Additional drawbacks include the ready emergence of resistant organisms, poor heat resistance, and efficacy that is rapid but not long-lasting. There is also a growing concern over the impact of such organic agents on the human body and the environment, which is why inorganic antibacterial agents are starting to become the norm.

Inorganic antibacterial/antifungal agents use primarily a material obtained by supporting metal ions such as silver, copper or zinc on a support. Examples of supports include zeolite, silica gel, calcium phosphate and zirconium phosphate. Compared with organic systems, features include the ability to exhibit effects against a broad range of microorganisms (broad antimicrobial spectrum) and a high thermal stability. However, given their low efficacy as antifungal agents, organic materials continue even today to account for the majority of antifungal agents.

Relevant prior-art literature is described in the following Patent Documents 1 to 6.

CITATION LIST

Patent Document 1: JP-A 2003-533588
Patent Document 2: JP-A 2003-113392
Patent Document 3: JP-A 2001-70423
Patent Document 4: JP-A 2001-37861
Patent Document 5: JP-A 2001-178806
Patent Document 6: JP-A 2005-318999

DISCLOSURE OF INVENTION

It is therefore an object of the present invention to provide a deodorizing/antibacterial/antifungal agent that gives a highly transparent thin film which has deodorizing properties and also exhibits antibacterial/antifungal properties, a method for preparing such an agent, and a member having the deodorizing/antibacterial/antifungal agent on a surface thereof.

As a result of extensive investigations, we have discovered that a deodorizing/antibacterial/antifungal agent composed of a mixture of two kinds of fine particles, deodorizing titanium oxide fine particles and antibacterial/antifungal metal-containing alloy fine particles, can easily produce a thin film that exhibits high deodorizing/antibacterial/antifungal properties and has a high transparency.

Accordingly, in one aspect, the invention provides a deodorizing/antibacterial/antifungal agent that includes a mixture of the following two kinds of fine particles: (i) titanium oxide fine particles, and (ii) alloy fine particles containing an antibacterial/antifungal metal.

The antibacterial/antifungal metal contained in the alloy fine particles (ii) is preferably at least one metal selected from the group consisting of silver, copper and zinc, and more preferably includes at least silver.

The amount of antibacterial/antifungal metal contained in the alloy fine particles (ii) is preferably from 1 to 100 wt % based on the total weight of the alloy fine particles.

The mixture of titanium oxide fine particles (i) and antibacterial/antifungal metal-containing alloy fine particles (ii) preferably has a volume-based 50% cumulative distribution size ($D_{50}$), as measured by dynamic laser light scattering, of from 5 to 100 nm.

The deodorizing/antibacterial/antifungal agent may further include a binder, which binder is preferably a silicon compound-based binder.

In a second aspect, the invention provides a member having on a surface thereof the deodorizing/antibacterial/antifungal agent of the first aspect of the invention.

In a third aspect, the invention provides a method for producing a deodorizing/antibacterial/antifungal agent, which method includes the steps of:

(1) preparing a peroxotitanic acid solution from a starting titanium compound, a basic substance, hydrogen peroxide and an aqueous dispersion medium;

(2) preparing a titanium oxide fine-particle dispersion by heating the peroxotitanic acid solution prepared in Step (1) at between 80 and 250° C. under pressure control;

(3) preparing a solution containing a starting antibacterial/antifungal metal compound and a solution containing a reducing agent for reducing the starting metal compound;

(4) preparing an alloy fine-particle dispersion by mixing together the solution containing a starting antibacterial/antifungal metal compound and the solution containing a reducing agent for reducing the starting metal compound that were prepared in Step (3);

(5) washing the alloy fine-particle dispersion prepared in Step (4) with an aqueous dispersion medium by membrane filtration method; and (6) mixing together the titanium oxide fine-particle dispersion and the alloy fine-particle dispersion obtained in Steps (2) and (5).

ADVANTAGEOUS EFFECTS OF THE INVENTION

This invention makes it possible to provide deodorizing/antibacterial/antifungal agents that give thin films of high transparency which confer deodorizing properties and also exhibit antibacterial/antifungal properties. A method for preparing such agents, and members having such a deodorizing/antibacterial/antifungal agent on a surface thereof can also be provided.

DESCRIPTION OF THE PREFERRED EMBODIMENTS

The objects, features and advantages of the invention will become more apparent from the following detailed description.

The deodorizing/antibacterial/antifungal agent of the invention includes a mixture of the following two kinds of fine particles: (i) titanium oxide fine particles, and (ii) alloy fine particles containing an antibacterial/antifungal metal, and may be used in a form obtained by dispersing the two kinds of fine particles in an aqueous dispersion medium. As subsequently described, this agent can be produced by mixing together two different, separately prepared, fine-particle dispersions: a titanium oxide fine-particle dispersion, and an antibacterial/antifungal metal-containing alloy fine-particle dispersion.

Titanium Oxide Fine-Particle Dispersion

Titanium oxide fine particles are generally known to have three crystal phases: rutile, anatase and brookite. The use of chiefly anatase or rutile is preferred. Here, "chiefly" means generally at least 50 wt %, preferably at least 70 wt %, and more preferably at least 90 wt %, and may even be 100 wt %, of all the titanium oxide fine-particle crystals.

To increase the deodorizing ability of the titanium oxide fine particles, a metal oxide of platinum, gold, palladium, iron, copper, nickel or the like may be supported on the titanium oxide fine particles, or the titanium oxide fine particles may be doped with an element such as tin, nitrogen, sulfur, carbon or a transition metal.

An aqueous solvent is typically used as the aqueous dispersion medium in the titanium oxide fine-particle dispersion. The use of water is preferred, although a mixed solvent of water and a hydrophilic organic solvent that mixes with water in any ratio may be used. The water is preferably, for example, deionized water, distilled water, or purified water. The hydrophilic organic solvent is preferably, for example, an alcohol such as methanol, ethanol or isopropanol; a glycol such as ethylene glycol; or a glycol ether such as ethylene glycol monomethyl ether, ethylene glycol monoethyl ether or propylene glycol n-propyl ether. When a mixed solvent is used, the proportion of hydrophilic organic solvent in the mixed solvent is preferably more than 0 wt % and up to 50 wt %, more preferably 20 wt % or less, and even more preferably 10 wt % or less.

The titanium oxide fine particles (i) in the titanium oxide fine-particle dispersion have a volume-based 50% cumulative distribution size ($D_{50}$) as measured by dynamic laser light scattering (also referred to below as the "average particle size") of preferably from 5 to 30 nm, and more preferably from 5 to 20 nm. At an average particle size below 5 nm, the deodorizing ability may be inadequate; at more than 30 nm, the dispersion may become opaque. Instruments that may be used to measure the average particle size include, for example, the ELSZ-2000ZS (Otsuka Electronics Co., Ltd.), the Nanotrac UPA-EX150 (Nikkiso Co., Ltd.) and the LA-910 (Horiba, Ltd.).

In terms of the ease of producing the subsequently described titanium oxide/alloy thin film of the required thickness, the concentration of titanium oxide fine particles in the titanium oxide fine-particle dispersion is preferably from 0.01 to 30 wt %, and more preferably from 0.5 to 20 wt %.

Here, using the formula shown below, the concentration of the titanium oxide fine-particle dispersion can be calculated from the weight of nonvolatile matter (titanium oxide fine particles) remaining when a portion of the titanium oxide fine-particle dispersion is sampled and heated at 105° C. for 3 hours to evaporate off the solvent and from the weight of the sampled titanium oxide fine-particle dispersion.

Concentration (%) of titanium oxide fine-particle dispersion=[weight of nonvolatile matter (g)/ weight of titanium oxide fine-particle dispersion (g)]×100

Antibacterial/Antifungal Metal-Containing Alloy Fine-Particle Dispersion

In this invention, the alloy fine particles are made of two or more different metal constituents, including at least one metal constituent which increases the antibacterial/antifungal properties.

Here, the "metal constituent which increases the antibacterial/antifungal properties" refers to a metal constituent that is harmful to microorganisms such as bacteria and fungi but is relatively harmless to the human body. Illustrative examples include, when particles of the metal constituent are coated onto a film and the test stipulated in JIS Z 2801 (Antibacterial Treated Products: Test of Antibacterial Activity and Efficacy) is carried out, metals for which reductions in the viable cell counts of *Staphylococcus aureus* and *Escherichia coli* are observed, such as silver, copper, zinc, platinum, palladium, nickel, aluminum, titanium, cobalt, zirconium, molybdenum and tungsten (see, for example: Miyano: *Tetsu to Hagane* 93(2007), No. 1, 57-65; and H. Kawakami: *ISIJ International* 48 (2008), No. 9, 1299-1304).

The alloy fine particles of the invention are preferably made of an alloy containing at least one of these metals, and more preferably an alloy containing at least one metal from among silver, copper and zinc.

More specific examples include alloy fine particles containing a combination of metal constituents, such as silver-copper, silver-palladium, silver-platinum, silver-tin, gold-copper, silver-nickel, silver-antimony, silver-copper-tin, gold-copper-tin, silver-nickel-tin, silver-antimony-tin, platinum-manganese, silver-titanium, copper-tin, cobalt-copper, zinc-magnesium, silver-zinc, copper-zinc and silver-copper-zinc.

Metal constituents other than those metal constituents which increase the antibacterial/antifungal properties within the alloy fine particles are not particularly limited. One or more may be selected from among gold, antimony, tin, sodium, magnesium, silicon, phosphorus, sulfur, potassium, calcium, scandium, vanadium, chromium, manganese, iron, gallium, germanium, arsenic, selenium, yttrium, niobium, technetium, ruthenium, rhodium, indium, tellurium, cesium, barium, hafnium, tantalum, rhenium, osmium, iridium, mercury, thallium, lead, bismuth, polonium, radium, lanthanum, cerium, praseodymium, neodymium, promethium, samarium, europium, gadolinium, actinium and thorium.

The content of metal constituents that increase the antibacterial/antifungal properties within the alloy fine particles may be set to from 1 to 100 wt %, preferably from 10 to 100 wt %, and more preferably from 50 to 100 wt %, of the total weight of the alloy fine particles. At less than 1 wt % of metal constituents that increase the antibacterial/antifungal properties, a sufficient antibacterial/antifungal performance may not be exhibited.

An aqueous solvent is generally used as the aqueous dispersion medium of the alloy fine-particle dispersion, with the use of water, a water-soluble organic solvent that is miscible with water, or a mixed solvent of water and a water-soluble organic solvent being preferred. Preferred examples of the water include deionized water, distilled water and pure water. Examples of water-soluble organic solvents include alcohols such as methanol, ethanol, n-propanol, 2-propanol, n-butanol, 2-butanol, tert-butanol, ethylene glycol, diethylene glycol and polyethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol n-propyl ether; ketones such as acetone and methyl ethyl ketone; water-soluble nitrogen-containing compounds such as 2-pyrrolidone and N-methylpyrrolidone; and ethyl acetate. These may be used singly, or two or more may be used in combination.

The dispersed particle size of the alloy fine particles (ii) in the alloy fine-particle dispersion, expressed as the volume-based 50% cumulative distribution size ($D_{50}$) measured by dynamic laser light scattering (also referred to below as "average particle size"), is preferably 200 nm or less, more preferably 100 nm or less, and even more preferably 70 nm or less. There is no particular lower limit to the average particle size and so use may theoretically be made of particles having a size down to the minimum size at which the particles are capable of having antibacterial/antifungal properties. However, a particle size of 1 nm or more is preferred for practical reasons. On the other hand, an average particle size in excess of 200 nm is undesirable because the dispersion becomes opaque. Instruments that may be used to measure the average particle size include, for example, the ELSZ-2000ZS (Otsuka Electronics Co., Ltd.), the Nanotrac UPA-EX150 (Nikkiso Co., Ltd.) and the LA-910 (Horiba, Ltd.).

The concentration of alloy fine particles in the alloy fine-particle dispersion is not particularly limited. However, because a lower concentration generally results in better dispersion stability, the concentration is preferably between 0.0001 and 10 wt %, more preferably between 0.001 and 5 wt %, and more preferably between 0.01 and 1 wt %. At a concentration below 0.0001 wt %, the productivity becomes very low, which is undesirable.

Titanium Oxide/Alloy Fine-Particle Dispersion

The titanium oxide/alloy fine-particle dispersion of the invention is obtained, as described above, by mixing together two different, separately prepared, fine-particle dispersions: a deodorizing titanium oxide fine-particle dispersion and an antibacterial/antifungal metal-containing alloy fine-particle dispersion.

Here, the dispersed particle size of the mixture of (i) deodorizing titanium oxide fine particles and (ii) antibacterial/antifungal metal-containing alloy fine particles in the titanium oxide/alloy fine-particle dispersion, expressed as the volume-based 50% cumulative distribution size ($D_{50}$) measured by dynamic laser light scattering (also referred to below as "average particle size"), is preferably from 5 to 100 nm, more preferably from 5 to 30 nm, and even more preferably from 5 to 20 nm. At an average particle size below 5 nm, the deodorizing ability may be inadequate. On the other hand, at an average particle size greater than 100 nm, the dispersion may become opaque.

The instrument for measuring the average particle size of the mixture of fine particles (i) and (ii) is the same as that described above.

The titanium oxide/alloy fine-particle dispersion of the invention may further include the subsequently described binder.

Method for Producing Deodorizing/Antibacterial/Antifungal Agent

The inventive method for producing a deodorizing/antibacterial/antifungal agent is one which ultimately obtains two types of fine particles, (i) deodorizing titanium oxide fine particles and (ii) antibacterial/antifungal metal-containing alloy fine particles, in a dispersed state within an aqueous dispersion medium. This method includes the following steps (1) to (6):

(1) preparing a peroxotitanic acid solution from a starting titanium compound, a basic substance, hydrogen peroxide and an aqueous dispersion medium;

(2) preparing a titanium oxide fine-particle dispersion by heating the peroxotitanic acid solution prepared in Step (1) at between 80 and 250° C. under pressure control;

(3) preparing a solution containing a starting antibacterial/antifungal metal compound and a solution containing a reducing agent for reducing the starting metal compound;

(4) preparing an alloy fine-particle dispersion by mixing together the solution containing a starting antibacterial/antifungal metal compound and the solution containing a reducing agent for reducing the starting metal compound prepared in Step (3);

(5) washing the alloy fine-particle dispersion prepared in Step (4) with an aqueous dispersion medium by membrane filtration method; and (6) mixing together the titanium oxide fine-particle dispersion and the alloy fine-particle dispersion obtained in Steps (2) and (5).

Steps (1) and (2) are steps for preparing the titanium oxide fine-particle dispersion.

Steps (3) to (5) are steps for preparing the alloy fine-particle dispersion. Although both physical methods and chemical methods exist, use is made in particular of liquid-phase reduction method, this being a chemical method for which the synthesis conditions are easy to adjust, which has broad controllable ranges in parameters such as composition, particle size and particle size distribution, and which has superior productivity. Liquid-phase reduction method mixes a reducing agent into a solution containing the two or more types of metal ions serving as the starting materials for the alloy, inducing the precipitation of alloy fine particles. The dispersibility of the alloy fine particles in the solvent can be further enhanced by also having an alloy fine-particle protecting agent be present within the reaction system at this time.

Step (6) ultimately prepares a titanium oxide/alloy fine-particle dispersion having deodorizing/antibacterial/antifungal properties by mixing together the titanium oxide fine-particle dispersion prepared in Step (2) and the alloy fine-particle dispersion obtained in Step (5).

The individual steps are described in detail below.
Step (1):
In Step (1) a peroxotitanic acid solution is prepared by reacting a starting titanium compound, a basic substance and hydrogen peroxide in an aqueous dispersion medium.

The reaction method may be either a method that adds the basic substance to the starting titanium compound within the aqueous dispersion medium to form titanium hydroxide, removes impurity ions other than the metallic ions to be included, and adds hydrogen peroxide to form peroxotitanic acid; or a method that adds hydrogen peroxide to the starting titanium compound and then adds the basic substance to form a peroxotitanium hydrate, removes impurities other than the metal ions to be included, and adds further hydrogen peroxide to form peroxotitanic acid.

Examples of the starting titanium compound include chlorides, nitrates, sulfates and other inorganic acid salts of titanium; formic acid, citric acid, oxalic acid, lactic acid, glycolic acid and other organic acid salts of titanium; and the titanium hydroxide that is made to settle out by adding an alkali to aqueous solutions of the foregoing salts and carrying out hydrolysis. Such starting titanium compounds may be used singly or two or more may be used in combination. Of these, the use of titanium chlorides ($TiCl_3$, $TiCl_4$) is preferred.

The above-mentioned aqueous dispersion media may be used in the manner formulated above as the aqueous dispersion medium. The concentration of the aqueous solution of starting titanium compound formed of the starting titanium compound and the aqueous dispersion medium is preferably 60 wt % or less, and more preferably 30 wt % or less. The concentration lower limit is suitably selected, although in general it is preferably at least 1 wt %.

The purpose of the basic substance is to smoothly convert the starting titanium compound into titanium hydroxide. Illustrative examples include hydroxides of alkali metals or alkaline earth metals, such as sodium hydroxide and potassium hydroxide; and amine compounds such as ammonia, alkanolamines and alkylamines. The basic substance is added and used in an amount such as to bring the pH of the aqueous solution of the starting titanium compound to 7 or above, and especially from 7 to 10. The basic substance may be used together with the aqueous dispersion medium after first being rendered into an aqueous solution of a suitable concentration.

The purpose of the hydrogen peroxide is to convert the starting titanium compound or titanium hydroxide into peroxotitanium—that is, a titanium oxide compound containing a Ti—O—O—Ti bond, and is typically used in the form of hydrogen peroxide water. The amount of hydrogen peroxide added is preferably set to from 1.5 to 20 moles per mole of titanium. When adding hydrogen peroxide and converting the starting titanium compound or titanium hydroxide into peroxotitanic acid, the reaction temperature is preferably set to between 5 and 80° C. and the reaction time is preferably set to from 30 minutes to 24 hours.

The resulting peroxotitanic acid solution may, for the sake of pH adjustment or the like, include an alkaline substance or an acidic substance. Illustrative examples of what are referred to here as alkaline substances include ammonia, sodium hydroxide, calcium hydroxide and alkylamines. Illustrative examples of acidic substances include inorganic acids such as sulfuric acid, nitric acid, hydrochloric acid, carbonic acid, phosphoric acid and hydrogen peroxide; and organic acids such as formic acid, citric acid, oxalic acid, lactic acid and glycolic acid. The pH of the peroxotitanic acid solution obtained at this time is from 1 to 9, with a pH of from 4 to 7 being preferred from the standpoint of safety during handling.
Step (2):
In Step (2), the peroxotitanic acid solution obtained in Step (1) is furnished to a hydrothermal reaction under pressure control and a temperature of between 80 and 250° C., preferably between 100 and 250° C., for a period of from 0.01 to 24 hours. From the standpoint of reaction efficiency and reaction controllability, a reaction temperature of between 80 and 250° C. is appropriate. As a result, the peroxotitanic acid is converted to titanium oxide fine particles. Here, "under pressure control" means to carry out suitable pressurization in such a way as to be able to maintain the reaction temperature in cases where the reaction temperature exceeds the boiling point of the dispersion medium. This includes control at atmospheric pressure in cases where the temperature is at or below the boiling point of the dispersion medium. The pressure used here is generally between about 0.12 MPa and about 4.5 MPa, preferably between about 0.15 MPa and about 4.5 MPa, and more preferably between about 0.20 MPa and about 4.5 MPa. The reaction time is preferably from 1 minute to 24 hours. Step (2) thus provides a deodorizing titanium oxide fine-particle dispersion.

The size of the resulting titanium oxide fine particles is preferably in the range already mentioned above. It is possible to control the particle size by adjusting the reaction conditions. For example, the particle size can be made smaller by shortening the reaction time or the temperature rise time.

Step (3):

In Step 3, a solution of a starting antibacterial/antifungal metal compound dissolved in an aqueous dispersion medium and a solution of a reducing agent for reducing this starting metal compound dissolved in an aqueous dispersion medium are prepared.

The method for preparing these solutions may be a method in which a starting antibacterial/antifungal metal compound and a reducing agent for reducing this starting metal compound are each separately added to an aqueous dispersion medium and dissolved by stirring. The stirring method is not particularly limited, so long as it is a method capable of effecting uniform dissolution in the aqueous dispersion medium. A commonly available stirrer may be used for this purpose.

Various antibacterial/antifungal metal compounds may be used as the starting antibacterial/antifungal metal compound. Examples include inorganic acid salts (e.g., chlorides, nitrates, sulfates), organic acid (e.g., formic acid, citric acid, oxalic acid, lactic acid, glycolic acid) salts; and complex salts (e.g., ammine complexes, cyano complexes, halogeno complexes, hydroxy complexes) of antibacterial/antifungal metals. These may be used singly, or two or more may be used in combination. Of these, the use of inorganic acid salts such as chlorides, nitrates and sulfates is preferred.

Any of various reducing agents that can reduce the metal ions making up the starting antibacterial/antifungal metal compounds may be used without particular limitation. Examples include hydrazines such as hydrazine, hydrazine monohydrate, phenyl hydrazine and hydrazinium sulfate; amines such as dimethylaminoethanol, triethylamine, octylamine and dimethylaminoborane; organic acids such as citric acid, ascorbic acid, tartaric acid, malic acid, malonic acid and formic acid; alcohols such as methanol, ethanol, isopropyl alcohol, ethylene glycol, diethylene glycol, triethylene glycol, tetraethylene glycol and benzotriazole; hydrides such as sodium borohydride, lithium borohydride, lithium triethylborohydride, lithium aluminum hydride, diisobutylaluminum hydride, tributyltin hydride, lithium tri(sec-butyl)borohydride, potassium tri(sec-butyl)borohydride, zinc borohydride and sodium acetoxyborohydride; pyrrolidones such as polyvinyl pyrrolidone, 1-vinyl pyrrolidone, N-vinyl pyrrolidone and methyl pyrrolidone; reducing sugars such as glucose, galactose, mannose, fructose, sucrose, maltose, raffinose and stachyose; and sugar alcohols such as sorbitol. These may be used singly, or two or more may be used in combination. The aqueous dispersion medium that dissolves the reducing agent may be one similar to the aqueous dispersion medium used for the metal compound.

A protective agent may be added to the solution obtained by dissolving the reducing agent in an aqueous dispersion medium. The protective agent is not particularly limited, so long as it is one than can prevent the agglomeration of alloy particles that have been reduced and have settled out of solution. Use can be made of surfactants and organic compounds having the ability to function as dispersants. Illustrative examples include surfactants such as anionic surfactants, cationic surfactants and nonionic surfactants; water-soluble polymer compounds such as polyvinyl pyrrolidone, polyvinyl alcohol, polyethyleneimine, polyethylene oxide, polyacrylic acid and methylcellulose; aliphatic amine compounds such as ethanolamine, diethanolamine, triethanolamine and propanolamine; primary amine compounds such as butylamine, dibutylamine, hexylamine, cyclohexylamine, heptylamine, 3-butoxypropylamine, octylamine, nonylamine, decylamine, dodecylamine, hexadecylamine, oleylamine and octadecylamine; diamine compounds such as N,N-dimethylethylenediamine and N,N-diethylethylenediamine; and carboxylic acid compounds such as oleic acid.

Water, a water-soluble organic solvent that is miscible with water, and mixed solvents of water and a water-soluble organic solvent are preferred as the aqueous dispersion medium (aqueous solvent). The water is preferably, for example, deionized water, distilled water or pure water. Examples of the water-soluble organic solvent include alcohols such as methanol, ethanol, isopropanol, n-propanol, 2-propanol, n-butanol, 2-butanol, tert-butanol, ethylene glycol and diethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol n-propyl ether; ketones such as acetone and methyl ethyl ketone; water-soluble nitrogen-containing compounds such as 2-pyrrolidone and N-methylpyrrolidone; and ethyl acetate. The water-soluble organic solvent may be used singly, or two or more may be used in combination.

A basic substance or an acidic substance may be added to the solvent. Examples of basic substances include alkali metal hydroxides such as sodium hydroxide and potassium hydroxide; alkali metal carbonates such as sodium carbonate and potassium carbonate; alkali metal bicarbonates such as sodium bicarbonate and potassium bicarbonate; alkali metal alkoxides such as potassium tert-butoxide, sodium methoxide and sodium ethoxide; alkali metal salts of aliphatic hydrocarbons, such as butyl lithium; and amines such as triethylamine, diethylaminoethanol and diethylamine. Examples of acidic substances include inorganic acids such as aqua regia, hydrochloric acid, nitric acid and sulfuric acid; and organic acids such as formic acid, acetic acid, chloroacetic acid, dichloroacetic acid, oxalic acid, trifluoroacetic acid and trichloroacetic acid.

The concentrations of these two solutions are not particularly limited. However, in general, given the tendency to be able to, at a lower concentration, make the primary particle size of the individual alloy fine particles that form smaller, it is preferable to set the concentration within a suitable concentration range in accordance with the target range in the primary particle size.

The pH levels of these two solutions are not particularly limited and are preferably adjusted to suitable pH levels in accordance with, for example, the intended molar ratio of the metals within the alloy fine particles and the intended primary particle size.

Step (4):

In Step (4), the solution of starting antibacterial/antifungal metal compound dissolved in an aqueous dispersion medium and the solution of a reducing agent for reducing this metal compound dissolved in an aqueous dispersion medium, both of which were prepared in Step (3), are mixed together to prepare an alloy fine-particle dispersion.

The method for mixing these two solutions is not particularly limited, provided it is a method capable of uniformly mixing the two solutions. Exemplary methods include the following: method placing the metal compound solution and the reducing agent solution in a reaction vessel and stirring the reactor contents to effect mixture; method placing the metal compound solution in a reaction vessel and, under stirring of the reactor contents, adding the reducing agent solution dropwise and stirring to effect mixture; method placing the reducing agent solution in a reaction vessel and, under stirring of the reactor contents, adding the metal compound solution dropwise and stirring to effect mixture; and method continuously feeding the metal compound solution and the reducing agent solution volumetrically, and mixing them together in a reaction vessel or a microreactor.

The temperature during mixing is not particularly limited, and is preferably adjusted to a suitable temperature in accordance with, for example, the intended molar ratio of the metals within the alloy fine particles and the intended primary particle size.

Step (5):

In Step (5), the alloy fine-particle dispersion prepared in Step (4) is washed with an aqueous dispersion medium by membrane filtration method.

The aqueous dispersion medium used is preferably water, a water-soluble organic solvent that is miscible with water, or a mixed solvent of water and a water-soluble organic solvent. The water is preferably deionized water, distilled water, pure water or the like. Examples of the water-soluble organic solvent include alcohols such as methanol, ethanol, isopropanol, n-propanol, 2-propanol, n-butanol, 2-butanol, tert-butanol, ethylene glycol and diethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol n-propyl ether; ketones such as acetone and methyl ethyl ketone; water-soluble nitrogen-containing compounds such as 2-pyrrolidone and N-methylpyrrolidone; and ethyl acetate. The water-soluble organic solvent may be used singly, or two or more may be used in combination.

Membrane filtration method washes and separates out nonvolatile impurities other than the alloy fine particles, such as constituents other than metal within the starting metal compound, the reducing agent and the protective agent, from the fine-particle dispersion. Washing is carried out until the weight ratio between alloy fine particles and nonvolatile impurities (alloy fine particles/nonvolatile impurities) in the alloy fine-particle dispersion becomes preferably from 0.01 to 10, more preferably from 0.05 to 5, and even more preferably from 0.1 to 1. At a weight ratio below 0.01, the amount of impurities relative to the alloy fine particles is high, and so the resulting antibacterial/antifungal properties and deodorizing performance may be inadequate. At a weight ratio greater than 10, the alloy fine particle-dispersing stability may decrease, which is undesirable.

Determining Concentration of Metal Constituents in Alloy Fine-Particle Dispersion (ICP-OES)

The concentration of metal constituents in the alloy fine-particle dispersion can be measured by suitably diluting the alloy fine-particle dispersion with pure water and introducing it into an inductively coupled plasma emission spectrophotometer (available from Agilent Technologies Japan, Ltd. under the trade name Agilent 5110 ICP-OES).

Determining Concentration of Nonvolatile Impurities Other than Metal Constituents in Alloy Fine-Particle Dispersion The concentration of nonvolatile impurities other than metal constituents in the alloy fine-particle dispersion can be determined by measuring the weight of the nonvolatile matter (alloy fine particles+nonvolatile impurities) remaining when a portion of the alloy fine-particle dispersion is sampled and heated at 105° C. for 3 hours to evaporate off the solvent, calculating the concentration of nonvolatile matter from the weight of nonvolatile matter and the weight of the alloy fine-particle dispersion, and subtracting the metal constituent concentration determined above by ICP-OES from the concentration of nonvolatile matter.

Nonvolatile Impurity Concentration (%)=[nonvolatile matter weight (g)/alloy fine-particle dispersion weight (g)]×100 −[percent concentration of metal constituents in alloy fine-particle dispersion]

The membrane used in membrane filtration method is not particularly limited, provided it is one that can separate off alloy fine particles and nonvolatile impurities other than alloy fine particles from the alloy fine-particle dispersion. Examples include microfiltration membranes, ultrafiltration membranes and nanofiltration membranes. Membrane filtration method may be carried out using a membrane having a suitable pore size from among these.

The method of filtration used may be, for example, any of the following: centrifugal filtration, pressure filtration or crossflow filtration.

Regarding the shape of the filter membrane, use may be made of a membrane filter having a suitable morphology, such as a hollow-fiber, spiral, tubular or flat membrane.

The filter membrane material is not particularly limited, so long as it has durability to alloy fine-particle dispersions. The material used may be suitably selected from among, for example, organic membranes made of polyethylene, tetrafluoroethylene, polypropylene, cellulose acetate, polyacrylonitrile, polyimide, polysulfone or polyethersulfone; and inorganic membranes made of silica, alumina, zirconia or titania.

Specific examples of such filter membranes include Microza (Asahi Kasei Corporation), Amicon Ultra (Merck Millipore), Ultrafilter (Advantec Toyo) and MEMBRALOX (Nihon Pore KK).

Step (6):

In Step (6), the titanium oxide fine-particle dispersion obtained in Step (2) and the alloy fine-particle dispersion obtained in Step (5) are mixed together, giving a titanium oxide/alloy fine-particle dispersion having antibacterial/antifungal properties.

The method of mixture is not particularly limited, provided it is a method that uniformly mixes together the two dispersions. For example, mixing may be carried out by stirring using a commonly available stirrer.

The mixing proportions of the titanium oxide fine-particle dispersion and the alloy fine-particle dispersion, expressed as the weight ratio (titanium oxide fine particles/alloy fine particles) between the fine particles in the respective dispersions of titanium oxide fine particles and alloy fine particles, is between 1 and 100,000, preferably between 10 and 10,000, and even more preferably between 20 and 1,000. A ratio below 1 is undesirable because a sufficient deodorizing ability is not exhibited, and a ratio greater than 100,000 is undesirable because a sufficient antibacterial/antifungal ability is not exhibited.

The size of the dispersed particles in the mixture of titanium oxide fine particles and alloy fine particles within the titanium oxide/alloy fine-particle dispersion is represented as the volume-based 50% cumulative distribution size (D50) measured by dynamic laser light scattering (also referred to below as the "average particle size"), which is described above.

The instrument used to measure the average particle size is also as described above.

In terms of the ease of producing a titanium oxide/alloy thin film of the required thickness, the sum of the concentrations of the titanium oxide fine particles, alloy fine particles and nonvolatile impurities in the titanium oxide/alloy fine-particle dispersion thus prepared is, as mentioned above, preferably from 0.01 to 20 wt %, and more preferably from 0.5 to 10 wt %. With regard to adjusting the concentration, in cases where the concentration is higher than the desired concentration, the concentration can be lowered by adding aqueous dispersion medium to dilute the dispersion. In cases where the concentration is lower than desired, the concentration can be increased by evaporating off and removing by filtration some of the aqueous dispersion medium.

The concentration of the titanium oxide/alloy fine-particle dispersion can be calculated as follows from the weight of the nonvolatile matter (titanium oxide fine particles, alloy fine particles and nonvolatile impurities) remaining when a portion of the titanium oxide/alloy fine-particle dispersion is sampled and heated at 105° C. for 3 hours to evaporate off the solvent and the weight of the sampled titanium oxide/alloy fine-particle dispersion.

Concentration (%) of titanium oxide/alloy fine-particle dispersion=[weight of nonvolatile matter (g)/weight of titanium oxide/alloy fine-particle dispersion (g)]×100

A binder may be added to the titanium oxide/alloy fine-particle dispersion, both for the purpose of making the dispersion easier to apply to the surface of the subsequently described various types of members and also to make the fine particles readily adhering. Exemplary binders include metal compound-based binders that contain, for example, silicon, aluminum, titanium or zirconium, and organic resin-based binders that contain, for example, a fluoroplastic, acrylic resin or urethane resin.

The binder is added and used in a weight ratio of the binder to the titanium oxide/alloy fine particles, expressed as [binder/(titanium oxide fine particles+alloy fine particles)], of preferably between 0.01 and 99, more preferably between 0.1 and 9, and even more preferably between 0.4 and 2.5. At a weight ratio below 0.01, adherence of the titanium oxide fine particles to the surface of various types of members may be inadequate; at a weight ratio above 99, the deodorizing ability and antibacterial/antifungal activity may be inadequate.

In particular, to obtain an excellent titanium oxide/alloy thin film having a deodorizing ability and also an antibacterial/antifungal activity and a high transparency, it is desirable for a silicon compound-based binder to be added and used in a compounding ratio (weight ratio of silicon compound to titanium oxide fine particles+alloy fine particles) of preferably between 1:99 and 99:1, more preferably between 10:90 and 90:10, and even more preferably between 30:70 and 70:30. Here, the "silicon compound-based binder" refers to a colloidal dispersion, solution or emulsion of a silicon compound that is obtained by including a solid or liquid silicon compound in an aqueous dispersion medium. Illustrative examples include colloidal silica (preferred particle size, 1 to 150 nm); solutions of silicates; silane and siloxane hydrolyzate emulsions; silicone resin emulsions; and emulsions of copolymers of a silicone resin with another resin, such as silicone-acrylic resin copolymers and silicone-urethane resin copolymers.

In cases where such a binder that increases film formability is added, it is preferably added to a titanium oxide/alloy fine-particle dispersion whose concentration has been adjusted as described above, in such manner as to achieve the desired concentration following mixture of the added aqueous binder solution.

Member Having
Deodorizing/Antibacterial/Antifungal Agent on
Surface

The deodorizing/antibacterial/antifungal agent of the invention can form a deodorizing/antibacterial/antifungal thin film on the surface of various types of members by a method such as that of spraying into air or depositing on the target object a dispersion in which two types of fine particles are dispersed: (i) titanium oxide fine particles and (ii) antibacterial/antifungal metal-containing alloy fine particles. No particular limitation is imposed on the type of member. Materials of which the member may be composed include organic materials and inorganic materials. Such members may have a variety of shapes according to their respective purposes and applications.

Illustrative examples of organic materials include synthetic resin materials such as vinyl chloride resin (PVC), polyethylene (PE), polypropylene (PP), polycarbonate (PC), acrylic resin, polyacetal, fluoroplastic, silicone resin, ethylene-vinyl acetate copolymer (EVA), acrylonitrile-butadiene rubber (NBR), polyethylene terephthalate (PET), polyethylene naphthalate (PEN), polyvinyl butyral (PVB), ethylene-vinyl alcohol copolymer (EVOH), polyimide resin, polyphenylene sulfide (PPS), polyetherimide (PEI), polyetheretherimide (PEEI), polyetheretherketone (PEEK), melamine resin, phenolic resin and acrylonitrile-butadiene-styrene (ABS) resin; natural materials such as natural rubber; and semi-synthetic materials made of the above synthetic resin materials and natural materials. These materials may be rendered into products of a required shape and construction, such as films, sheets, textile materials, textile products and other moldings or laminates.

Examples of inorganic materials include nonmetallic inorganic materials and metallic inorganic materials. Examples of nonmetallic inorganic materials include glass, ceramic and stone. These may be rendered into products of various forms, such as tile, glass, mirrors, walls and decorative materials. Examples of metallic inorganic materials include cast iron, steel, iron, ferrous alloys, aluminum, aluminum alloys, nickel, nickel alloys and diecast zinc. These may be plated with the above metallic inorganic materials or coated with the above organic materials, or may be platings applied to the surface of the above organic materials or nonmetallic inorganic materials.

Of the various above members, the deodorizing/antibacterial/antifungal agent of the invention is especially useful for producing a transparent thin film of the deodorizing/antibacterial/antifungal agent on polymer films such as PET.

The method of forming a deodorizing/antibacterial/antifungal agent thin film on the surface of various types of members may be one in which the deodorizing/antibacterial/antifungal agent dispersion (titanium oxide/alloy fine-particle dispersion) is coated onto the surface of the member by a known coating method such as spray coating or dip coating, and then dried by a known drying method such as far-infrared drying, drying by induction heating or hot-air drying. The thickness of the titanium oxide/alloy thin film may be variously selected, although a thickness in the range of from 10 nm to 10 μm is generally preferred.

A coat of the above-described deodorizing/antibacterial/antifungal agent (titanium oxide/alloy fine particles) is formed in this way. In cases where binder is included in the above-indicated amount within the dispersion, a coat that contains titanium oxide/alloy fine particles and binder is formed.

The deodorizing/antibacterial/antifungal agent (titanium oxide/alloy) thin film that is formed in this way is transparent and has excellent deodorizing properties, in addition to which antibacterial/antifungal effects can be obtained. Various types of members on which such a deodorizing/antibacterial/antifungal agent thin film has been formed are able to exhibit surface cleaning, deodorizing, antibacterial and other effects.

EXAMPLES

The following Working Examples and Comparative Examples are provided to illustrate the invention, and are not intended to limit the scope thereof. In these Examples, the "starting antibacterial/antifungal metal compound" is sometimes abbreviated as "starting metal compound."

The various measurements in this invention were carried out as described below.

(1) Test of Deodorizing Ability of Titanium Oxide/Alloy Thin Film

The deodorizing ability of the titanium oxide/alloy fine-particle dispersion was tested in accordance with the deodorizing ability test described in the Japan Textile Technology Evaluation Council's JEC301 ("Certification Standards for SEK Mark Textile Products"). The samples were produced by spraying 2 g of a liquid coating for evaluation prepared from the titanium oxide/alloy fine-particle dispersion and binder onto a polyester fabric substrate (Kimtech Pure W3 Dry Wiper, from Nippon Paper Crecia Co., Ltd.) cut to a size of 100 mm square, and then drying. The results were rated according to the following criteria. Ten odor ingredients specified in these criteria were tested: ammonia, acetic acid, methyl mercaptan, hydrogen sulfide, acetaldehyde, pyridine, trimethylamine, nonenal, indole and isovaleric acid.

Excellent (Exc): Seven or more ingredients had odor ingredient loss ratios of ≥70%
Good: Five or more ingredients had odor ingredient loss ratios of ≥70%
Marginal: Three or more ingredients had odor ingredient loss ratios of ≥70%
Poor (NG): Two or fewer ingredients had odor ingredient loss ratios of ≥70%

(2) Test of Antibacterial Activity of Titanium Oxide/Alloy Thin Film

The antibacterial performance of the titanium oxide/alloy thin film was rated according to the criteria shown below for a sample obtained by applying a titanium oxide thin film to a thickness of 100 nm onto a 50 mm square glass substrate. The test was carried out in accordance with JIS Z 2801:2012 (Antibacterial Treated Products: Test of Antibacterial Activity and Efficacy).

Excellent (Exc): All antibacterial activity values are 4.0 or more
Good (Good): All antibacterial activity values are 2.0 or more
Poor (NG): Some antibacterial activity values are less than 2.0

(3) Test of Fungal Resistance of Titanium Oxide/Alloy Thin Film

Using a sample obtained by applying a titanium oxide/alloy thin film to a thickness of 100 nm onto a 50 mm square glass substrate, the antifungal performance of the titanium oxide/alloy thin film was evaluated for up to 8 weeks following application by a method in accordance with JIS Z 2911:2010 (Method for Testing Fungal Resistance). Evaluation was carried out according to the following criteria by rating the state of fungal growth as set forth in Appendix A.

Excellent (Exc): Fungal growth state is from 0 to 1
Good: Fungal growth state is from 2 to 3
Poor (NG): Fungal growth state is from 4 to 5

(4) Identification of Crystal Phases of Titanium Oxide Fine Particles

The crystal phases of the titanium oxide fine particles were identified by powder x-ray diffraction analysis (using the D2 PHASER desktop x-ray powder diffractometer from Bruker AXS) of the titanium oxide fine-particle powders recovered by drying the titanium oxide fine-particle dispersions at 105° C. for 3 hours.

(5) Transparency of Titanium Oxide/Alloy Thin Film

The haze (%) of the glass plate serving as the substrate was measured. The dispersion was then coated onto the glass and dried to form a titanium oxide/alloy thin film, and the haze of the glass plate on which this thin film has been formed was measured. The haze of the titanium oxide/alloy thin film itself was determined from the difference between these two measurements. Haze measurements were carried out using the NDH-200 digital haze meter from Nippon Denshoku Industries Co., Ltd. The transparency of the titanium oxide/alloy thin film was rated according to the following criteria from the difference in the haze measurements obtained.

Excellent (Exc): The difference was +1% or less
Good: The difference was more than +1% and up to +3%
Poor (NG): The difference was more than +3%

(6) Determination of Alloy Presence in Alloy Fine Particles

An assessment as to whether an alloy is indeed present in the alloy fine particles was carried out by energy-dispersive X-ray spectroscopy under observation with a scanning transmission electron microscope (ARM-200F, from JEOL Ltd.). Specifically, the alloy fine particle dispersion was added dropwise onto a carbon grid for transmission electron microscopy and, after removing the moisture by drying, was examined under magnification. A number of fields containing several particles regarded as having average shapes were selected and STEM-EDX mapping was carried out. In cases where it was confirmed that each of the metal constituents making up the alloy are detected within a single particle, the particles were judged to be alloy fine particles.

Working Example 1

Preparation of Titanium Oxide Fine-Particle Dispersion

A titanium hydroxide precipitate was obtained by diluting a 36 wt % aqueous solution of titanium(IV) chloride ten-fold with pure water and then gradually adding 10 wt % ammonia water to effect neutralization and hydrolysis. The pH of the solution at this time was 9. The resulting precipitate was deionization treated by the repeated addition of pure water and decantation. Next, 35 wt % hydrogen peroxide water was added to the deionized titanium hydroxide precipitate to a molar ratio $H_2O_2/Ti$ of 5, after which the system was stirred for one day at room temperature to fully carry out the reaction, thereby giving a clear, yellow-colored peroxotitanic acid solution (a).

A 500 mL autoclave was charged with 400 mL of the peroxotitanic acid solution (a), and this was hydrothermally treated at 130° C. and 0.5 MPa for 90 minutes. The concentration was then adjusted by adding pure water, giving a titanium oxide fine-particle dispersion (A) (nonvolatiles concentration, 1 wt %).

The results of various measurements on the titanium oxide fine-particle dispersions thus obtained are collectively presented in Table 1.

Preparation of Silver-Copper Alloy Fine-Particle Dispersion

A starting metal compound-containing solution (I) was obtained by dissolving silver nitrate to a silver concentration of 2.50 mmol/L and copper nitrate dihydrate to a copper concentration of 2.50 mmol/L in ethylene glycol as the solvent. The starting metal compound-containing solutions obtained are collectively shown in Table 2.

A reducing agent-containing solution (i) was obtained by mixing together 55 wt % of ethylene glycol and 8 wt % of pure water as solvents, 2 wt % of potassium hydroxide as the basic substance, 20 wt % of hydrazine monohydrate and 5 wt % of dimethylaminoethanol as the reducing agents, and 10 wt % of polyvinylpyrrolidone as a reducing agent/protective agent.

An alloy fine-particle dispersion (a) was obtained by rapidly mixing 0.2 L of reducing agent-containing solution (i) having a temperature of 25° C. into 2 L of starting metal compound-containing solution (I) that was heated to 160° C. in a reactor, and subjecting the resulting mixture to concentration and pure-water washing with an ultrafiltration membrane having a molecular weight cutoff of 10,000 (Microza, from Asahi Kasei Corporation). The alloy fine-particle dispersions obtained are collectively shown in Table 3.

A titanium oxide/alloy fine-particle dispersion (E-1) according to the invention was obtained by mixing together the titanium oxide fine-particle dispersion (A) and the alloy fine-particle dispersion (a) in such a way that the weight ratio between the respective fine particles (titanium oxide fine particles/alloy fine particles) in the dispersion became 100. The starting metal compound-containing solutions obtained are collectively shown in Table 4.

A liquid coating for evaluation was prepared by adding a silica-based binder (colloidal silica available under the trade name Snotex 20 from Nissan Chemical Industries Co., Ltd.; average particle size, 10 to 20 nm; an aqueous solution having a $SiO_2$ concentration of 20 wt %) to the titanium oxide/alloy fine-particle dispersion (E-1) such that the weight ratio $TiO_2/SiO_2$ became 1.5.

Test samples for the various evaluations were produced as described above from the liquid coating for evaluation, and the various evaluations were carried out.

The deodorizing ability test results are presented in Table 5, evaluation results for the antibacterial test and the antifungal test are presented in Table 6, and results for titanium oxide/alloy thin-film transparency are shown in Table 7.

Working Example 2

Preparation of Titanium Oxide Fine-Particle Dispersion

Aside from the adding and dissolving tin(IV) chloride in a 36 wt % aqueous titanium(IV) oxide solution so that Ti/Sn (molar ratio) became 20, a clear, yellow-colored peroxotitanic acid solution (b) was obtained in the same way as in Working Example 1.

A 500 mL autoclave was charged with 400 mL of the peroxotitanic acid solution (b), and this was hydrothermally treated at 150° C. for 90 minutes. The concentration was then adjusted by adding pure water, thereby giving a titanium oxide fine-particle dispersion (B) (nonvolatiles concentration, 1.0 wt %).

Preparation of Silver-Copper Alloy Fine-Particle Dispersion

Aside from using a starting metal compound-containing solution (II) obtained by dissolving silver nitrate to a silver concentration of 4.50 mmol/L and copper nitrate dihydrate to a copper concentration of 0.50 mmol/L in ethylene glycol as the solvent, an alloy fine-particle dispersion (β) was obtained in the same way as in Working Example 1.

The titanium oxide fine-particle dispersion (B) and the alloy fine-particle dispersion (β) were mixed together such that the weight ratio of fine particles in the respective dispersions (titanium oxide fine particles/alloy fine particles) became 800, thereby giving a titanium oxide/alloy fine-particle dispersion (E-2) according to the invention.

Evaluation samples were produced and various evaluations were carried out in the same way as in Working Example 1.

Working Example 3

Preparation of Silver-Palladium Alloy Fine-Particle Dispersion

Aside from using a starting metal compound-containing solution (III) obtained by dissolving silver nitrate to a silver concentration of 4.00 mmol/L and palladium nitrate dihydrate to a palladium concentration of 1.00 mmol/L in pure water as the solvent, an alloy fine-particle dispersion (γ) was obtained in the same way as in Working Example 1.

The titanium oxide fine-particle dispersion (A) and the alloy fine-particle dispersion (γ) were mixed together such that the weight ratio of fine particles in the respective dispersions (titanium oxide fine particles/alloy fine particles) became 200, thereby giving a titanium oxide/alloy fine-particle dispersion (E-3) according to the invention.

Evaluation samples were produced and the various evaluations were carried out in the same way as in Working Example 1.

Working Example 4

Preparation of Silver-Platinum Alloy Fine-Particle Dispersion

Aside from using a starting metal compound-containing solution (IV) obtained by dissolving silver nitrate to a silver concentration of 4.00 mmol/L and chloroplatinic acid hexahydrate to a platinum concentration of 1.00 mmol/L in ethylene glycol as the solvent, an alloy fine-particle dispersion (δ) was obtained in the same way as in Working Example 1.

The titanium oxide fine-particle dispersion (A) and the alloy fine-particle dispersion (δ) were mixed together such that the weight ratio of fine particles in the respective dispersions (titanium oxide fine particles/alloy fine particles) became 1,000, thereby giving a titanium oxide/alloy fine-particle dispersion (E-4) according to the invention.

Evaluation samples were produced and the various evaluations were carried out in the same way as in Working Example 1.

Working Example 5

Preparation of Copper-Zinc Alloy Fine-Particle Dispersion

Aside from using a starting metal compound-containing solution (V) obtained by dissolving copper nitrate trihydrate to a copper concentration of 3.75 mmol/L and zinc chloride hexahydrate to a zinc concentration of 1.25 mmol/L in ethylene glycol as the solvent, an alloy fine-particle dispersion (ε) was obtained in the same way as in Working Example 1.

The titanium oxide fine-particle dispersion (A) and the alloy fine-particle dispersion (ε) were mixed together such that the weight ratio of fine particles in the respective dispersions (titanium oxide fine particles/alloy fine particles) became 300, thereby giving a titanium oxide/alloy fine-particle dispersion (E-5) according to the invention.

Evaluation samples were produced and the various evaluations were carried out in the same way as in Working Example 1.

Working Example 6

Preparation of Silver-Zinc Alloy Fine-Particle Dispersion

Aside from using a starting metal compound-containing solution (VI) obtained by dissolving silver nitrate to a silver concentration of 3.75 mmol/L and zinc nitrate hexahydrate to a zinc concentration of 1.25 mmol/L in ethylene glycol as the solvent, an alloy fine-particle dispersion (ζ) was obtained in the same way as in Working Example 1.

The titanium oxide fine-particle dispersion (A) and the alloy fine-particle dispersion (ζ) were mixed together such that the weight ratio of fine particles in the respective dispersions (titanium oxide fine particles/alloy fine particles) became 300, thereby giving a titanium oxide/alloy fine-particle dispersion (E-6) according to the invention.

Evaluation samples were produced and the various evaluations were carried out in the same way as in Working Example 1.

Working Example 7

Preparation of Zinc-Magnesium Alloy Fine-Particle Dispersion

Aside from using a starting metal compound-containing solution (VII) obtained by dissolving zinc nitrate hexahydrate to a zinc concentration of 3.75 mmol/L and magnesium nitrate hexahydrate to a magnesium concentration of 1.25 mmol/L in ethylene glycol as the solvent, an alloy fine-particle dispersion (η) was obtained in the same way as in Working Example 1.

The titanium oxide fine-particle dispersion (A) and the alloy fine-particle dispersion (η) were mixed together such that the weight ratio of fine particles in the respective dispersions (titanium oxide fine particles/alloy fine particles) became 300, thereby giving a titanium oxide/alloy fine-particle dispersion (E-7) according to the invention.

Evaluation samples were produced and the various evaluations were carried out in the same way as in Working Example 1.

Working Example 8

Preparation of Silver-Copper Alloy Fine-Particle Dispersion

Aside from changing the concentration/pure-water washing proportions with an ultrafiltration membrane having a molecular weight cutoff of 10,000 (Microza, Asahi Kasei Corporation), an alloy fine particle dispersion (θ) was obtained in the same way as in Working Example 1.

The titanium oxide fine-particle dispersion (A) and the alloy fine-particle dispersion (θ) were mixed together such that the weight ratio of fine particles in the respective dispersions (titanium oxide fine particles/alloy fine particles) became 100, thereby giving a titanium oxide/alloy fine-particle dispersion (E-8) according to the invention.

Evaluation samples were produced and the various evaluations were carried out in the same way as in Working Example 1.

Working Example 9

The titanium oxide fine-particle dispersion (A) and the alloy fine-particle dispersion (α) were mixed together in such a way that the weight ratio between the fine particles in the respective dispersion (titanium oxide fine particles/alloy fine particles) became 5,000, thereby giving a titanium oxide/alloy fine-particle dispersion (E-9) according to the invention.

Evaluation samples were produced and the various evaluations were carried out in the same way as in Working Example 1.

Working Example 10

Preparation of Silver-Tin Alloy Fine-Particle Dispersion

Aside from using a starting metal compound-containing solution (IX) obtained by dissolving silver nitrate to a silver concentration of 1.50 mmol/L and tin chloride to a tin concentration of 3.5 mmol/L in ethylene glycol as the solvent, an alloy fine-particle dispersion (ι) was obtained in the same way as in Working Example 1.

The titanium oxide fine-particle dispersion (A) and the alloy fine-particle dispersion (ι) were mixed together such that the weight ratio of fine particles in the respective dispersions (titanium oxide fine particles/alloy fine particles) became 100, thereby giving a titanium oxide/alloy fine-particle dispersion (E-10) according to the invention.

Evaluation samples were produced and the various evaluations were carried out in the same way as in Working Example 1.

Comparative Example 1

A titanium oxide fine-particle dispersion (C-1) was obtained from the titanium oxide fine-particle dispersion (A) alone.

A liquid coating for evaluation was prepared by adding a silica-based binder (colloidal silica available under the trade name Snotex 20 from Nissan Chemical Industries Co., Ltd.; average particle size, 10 to 20 nm; an aqueous solution having a $SiO_2$ concentration of 20 wt %) to the titanium oxide fine-particle dispersion (C-1) so as to give a weight ratio $TiO_2/SiO_2$ of 1.5.

Test samples for the various evaluations were produced as described above from the liquid coating for evaluation, and the evaluations were carried out.

Comparative Example 2

An alloy fine particle dispersion (C-2) was obtained from alloy fine-particle dispersion (α) alone.

Evaluation samples were produced and the various evaluations were carried out in the same way as in Working Example 1.

Comparative Example 3

Preparation of Silver Fine-Particle Dispersion

A starting metal compound-containing solution (X) was obtained by dissolving silver nitrate to a silver concentration of 4.00 mmol/L in ethylene glycol as the solvent.

Aside from using the starting metal compound-containing solution (X), a silver fine-particle dispersion (κ) was obtained in the same way as in Working Example 1.

The titanium oxide fine-particle dispersion (A) and the silver fine-particle dispersion (κ) were mixed together such that the weight ratio of fine particles in the respective dispersions (titanium oxide fine particles/silver fine particles) became 300, thereby giving a titanium oxide/silver fine-particle dispersion (C-3).

Evaluation samples were produced and the various evaluations were carried out in the same way as in Working Example 1.

Comparative Example 4

Preparation of Starting Silver Solution

A starting silver compound-containing solution (XI) was obtained by dissolving silver nitrate to a silver concentration of 4.00 mmol/L in pure water as the solvent.

The titanium oxide fine-particle dispersion (A) and the starting silver compound-containing solution (XI) were mixed together such that the weight ratio of fine particles in the respective dispersions (titanium oxide fine particles/silver constituent) became 300, thereby giving a titanium oxide/silver fine-particle dispersion (C-4).

Evaluation samples were produced and the various evaluations were carried out in the same way as in Working Example 1.

As is apparent from Comparative Example 1, a titanium oxide fine-particle dispersion by itself does not exhibit antibacterial/antifungal properties.

As is apparent from Comparative Example 2, an alloy fine powder dispersion by itself does not exhibit a deodorizing ability and has a weak antifungal activity.

As is apparent from Comparative Example 3, a titanium oxide/silver fine-particle dispersion containing a mixture of titanium oxide fine particles and silver fine particles has a weak deodorizing ability and a weak antifungal activity.

As is apparent from Comparative Example 4, when a silver solution was added to titanium oxide fine particles, the particle size in the titanium oxide fine-particle dispersion increased, resulting in a decline in transparency, in addition to which the deodorizing ability and the antifungal activity were weak.

Field Test of Titanium Oxide/Alloy Thin Film in Public Restroom

A field test of titanium oxide/alloy thin films was carried out in a public restroom at a train station. A titanium oxide/alloy thin film was applied to a thickness of 100 nm to the walls and floor of the restroom. At each measurement point, the odor and viable cell count were checked before treatment, after cleaning, shortly following application of the titanium oxide/alloy thin film, and again four weeks and ten weeks following application. Evaluation was carried out using the samples from Working Example 1 and Comparative Example 1.

The odor was measured with an odor sensor (XP-329 IIIR Odor Level Indicator, from New Cosmos Electric Co., Ltd.) and evaluated based on the level indication value. The level indication value indicates the odor strength on a scale of 0 to 2,000, with a larger value signifying a stronger odor. Unlike concentration values, these numerical values are not absolute values. Rather, they are relative values based on comparison with similar odors. The measurement points were located on sinks, on urinal shelves, and inside toilet stalls. The evaluation results are presented in Table 8.

Viable cell counts were determined by visually counting the number of red colonies that formed on the surface of the growth medium when a total cell count measuring device (San-Ai Biochecker-TTC, from San-Ai Oil Co., Ltd.) was attached for 3 seconds to the surface to be evaluated, followed by incubation at 37° C. for 24 hours. A smaller number of colonies indicates few viable cells on the evaluated surface; i.e., high antibacterial/antifungal properties. The measurement points were the walls along the sinks, the walls/floors along the urinals, and the walls/floors of the toilet stalls. The evaluation results are presented in Table 9.

The field test results obtained in Working Example 1 and Comparative Example 1 show that, based on comparison of the results obtained prior to treatment with the results obtained after cleaning, the odor and viable cell count do not sufficiently decline merely with ordinary cleaning. It was confirmed that by applying a liquid coating composed of the titanium oxide/alloy fine-particle dispersion of the invention after cleaning, the odor and viable cell count greatly decline and that this state is maintained even after four weeks and ten weeks have elapsed.

On the other hand, the odor and viable cell count-reducing effects when a liquid coating composed solely of a titanium oxide fine-particle dispersion was applied were found to be low.

TABLE 1

| Titanium oxide fine-particle dispersion | Nonvolatiles concentration (wt %) | Average particle size $D_{50}$ (nm) | Crystal phase |
|---|---|---|---|
| (A) | 1.0 | 12 | anatase |
| (B) | 1.0 | 9 | rutile |

TABLE 2

| Starting metal compound-containing solution | Solvent 1 | Alloy constituent 1 | Concentration (mmol/L) | Alloy constituent 2 | Concentration (mmol/L) | Antibacterial/antifungal metal ratio (%) |
|---|---|---|---|---|---|---|
| (I) | ethylene glycol | $AgNO_3$ | 2.50 | $Cu(NO_3)_2 \cdot 3H_2O$ | 2.50 | 100 |
| (II) | ethylene glycol | $AgNO_3$ | 4.50 | $Cu(NO_3)_2 \cdot 3H_2O$ | 0.50 | 100 |
| (III) | pure water | $AgNO_3$ | 4.00 | $Pd(NO_3)_2 \cdot 2H_2O$ | 1.00 | 100 |
| (IV) | ethylene glycol | $AgNO_3$ | 4.00 | $H_2[PtCl_6] \cdot 6H_2O$ | 1.00 | 80 |
| (V) | ethylene glycol | $Cu(NO_3)_2 \cdot 3H_2O$ | 3.75 | $Zn(NO_3)_2 \cdot 6H_2O$ | 1.25 | 100 |
| (VI) | ethylene glycol | $AgNO_3$ | 3.75 | $Zn(NO_3)_2 \cdot 6H_2O$ | 1.25 | 100 |
| (VII) | ethylene glycol | $Zn(NO_3)_2 \cdot 6H_2O$ | 3.75 | $Mg(NO_3)_2 \cdot 6H_2O$ | 1.25 | 75 |
| (IX) | ethylene glycol | $AgNO_3$ | 1.50 | $SnCl_2$ | 3.50 | 30 |
| (X) | ethylene glycol | $AgNO_3$ | 4.00 | — | — | 100 |
| (XI) | pure water | $AgNO_3$ | 4.00 | — | — | 100 |

TABLE 3

| Alloy fine-particle dispersion | Nonvolatiles content (wt %) | Alloy fine particles (wt %) | Alloy fine particles/nonvolatile impurities | Average particle size $D_{50}$ (nm) |
|---|---|---|---|---|
| (α) | 0.70 | 0.20 | 0.40 | 60 |
| (β) | 0.71 | 0.12 | 0.20 | 35 |
| (γ) | 0.65 | 0.10 | 0.18 | 53 |
| (δ) | 1.00 | 0.30 | 0.43 | 60 |
| (ε) | 0.60 | 0.08 | 0.15 | 49 |
| (ζ) | 0.60 | 0.08 | 0.15 | 45 |
| (η) | 0.60 | 0.08 | 0.15 | 68 |
| (θ) | 0.70 | 0.05 | 0.08 | 30 |
| (ι) | 0.70 | 0.15 | 0.27 | 61 |
| (κ) | 0.70 | 0.10 | 0.17 | 75 |

TABLE 4

| Titanium oxide/alloy fine-particle dispersion | Titanium oxide fine-particle dispersion | Alloy fine-particle dispersion | Titanium oxide fine particles/alloy fine particles | Nonvolatile concentration (%) | Average particle size $D_{50}$ (nm) |
|---|---|---|---|---|---|
| (E-1) | (A) | (α) | 100 | 1.0 | 18 |
| (E-2) | (B) | (β) | 800 | 1.0 | 14 |
| (E-3) | (A) | (γ) | 200 | 1.0 | 16 |
| (E-4) | (A) | (δ) | 1,000 | 1.0 | 17 |
| (E-5) | (A) | (ε) | 300 | 1.0 | 16 |
| (E-6) | (A) | (ζ) | 300 | 1.0 | 16 |
| (E-7) | (A) | (η) | 300 | 1.0 | 19 |
| (E-8) | (A) | (θ) | 100 | 0.8 | 15 |
| (E-9) | (A) | (α) | 5,000 | 1.0 | 15 |
| (E-10) | (A) | (ι) | 100 | 0.9 | 18 |
| (C-1) | (A) | — | — | 1.0 | 12 |
| (C-2) | — | (α) | — | 0.7 | 60 |

TABLE 4-continued

| Titanium oxide/ alloy fine-particle dispersion | Titanium oxide fine-particle dispersion | Alloy fine-particle dispersion | Titanium oxide fine particles/ alloy fine particles | Nonvolatile concentration (%) | Average particle size $D_{50}$ (nm) |
|---|---|---|---|---|---|
| (C-3) | (A) | (κ) | 300 | 1.0 | 22 |
| (C-4) | (A) | (XI) | 300 | 0.9 | 56 |

TABLE 5

| | | Percent reduction in odor ingredients | | | | | | | | | Evaluation | |
|---|---|---|---|---|---|---|---|---|---|---|---|---|
| | | Ammonia | Acetic acid | Hydrogen sulfide | Methyl mercaptan | Trimethylamine | Acetaldehyde | Pyridine | Isovaleric acid | Nonenal | Indole | Number of odor ingredients with loss ratios ≥70% | Rating |
| Working Example | 1 | 82 | 95 | 75 | 35 | 95 | 18 | 83 | 96 | 90 | 100 | 8 | Exc |
| | 2 | 80 | 92 | 72 | 30 | 91 | 16 | 81 | 92 | 92 | 100 | 8 | Exc |
| | 3 | 76 | 88 | 70 | 28 | 86 | 16 | 82 | 88 | 91 | 98 | 8 | Exc |
| | 4 | 60 | 72 | 55 | 20 | 73 | 5 | 65 | 74 | 75 | 75 | 5 | good |
| | 5 | 71 | 85 | 61 | 21 | 84 | 15 | 78 | 85 | 82 | 91 | 7 | Exc |
| | 6 | 73 | 82 | 62 | 23 | 81 | 13 | 76 | 83 | 81 | 85 | 7 | Exc |
| | 7 | 75 | 78 | 63 | 25 | 75 | 10 | 69 | 79 | 73 | 82 | 6 | good |
| | 8 | 62 | 75 | 50 | 18 | 71 | 4 | 62 | 74 | 70 | 76 | 5 | good |
| | 9 | 61 | 76 | 48 | 17 | 73 | 5 | 64 | 71 | 74 | 71 | 5 | good |
| | 10 | 60 | 71 | 43 | 15 | 70 | 3 | 60 | 73 | 71 | 72 | 5 | good |
| Comparative Example | 1 | 69 | 75 | 63 | 24 | 80 | 12 | 79 | 86 | 81 | 87 | 6 | good |
| | 2 | 43 | 63 | 26 | 12 | 24 | 3 | 58 | 68 | 48 | 69 | 0 | NG |
| | 3 | 62 | 76 | 66 | 17 | 72 | 5 | 60 | 72 | 68 | 73 | 4 | marginal |
| | 4 | 52 | 70 | 52 | 12 | 67 | 8 | 64 | 72 | 67 | 70 | 3 | marginal |

TABLE 6

| | | Test of antibacterial performance | | | Test of antifungal performance | | | |
|---|---|---|---|---|---|---|---|---|
| | | Antibacterial activity | | | Fungal growth state (4 weeks) | Evaluation | Fungal growth state (8 weeks) | Evaluation |
| | | *Escherichia coli* | *Staphylococcus aureus* | Evaluation | | | | |
| Working Example | 1 | 5.2 | 4.6 | Exc | 0 | Exc | 1 | Exc |
| | 2 | 4.8 | 4.3 | Exc | 1 | Exc | 1 | Exc |
| | 3 | 5.0 | 4.5 | Exc | 0 | Exc | 1 | Exc |
| | 4 | 4.3 | 3.7 | good | 2 | good | 2 | good |
| | 5 | 4.5 | 4.0 | Exc | 1 | Exc | 2 | good |
| | 6 | 4.6 | 4.1 | Exc | 1 | Exc | 2 | good |
| | 7 | 4.1 | 3.6 | Exc | 2 | good | 2 | good |
| | 8 | 3.9 | 3.3 | good | 2 | good | 3 | good |
| | 9 | 3.3 | 2.7 | good | 3 | good | 3 | good |
| | 10 | 3.6 | 3.1 | good | 2 | good | 3 | good |
| Comparative Example | 1 | 0.0 | 0.0 | NG | 4 | NG | 5 | NG |
| | 2 | 5.1 | 4.6 | Exc | 3 | good | 4 | NG |
| | 3 | 3.9 | 2.4 | good | 3 | good | 4 | NG |
| | 4 | 4.1 | 2.6 | good | 4 | NG | 4 | NG |

TABLE 7

| | | Transparency of titanium oxide/alloy thin film | |
|---|---|---|---|
| | | Haze (%) | Evaluation |
| Working Example | 1 | 0.4 | good |
| | 2 | 0.2 | good |
| | 3 | 0.3 | good |
| | 4 | 0.3 | good |
| | 5 | 0.3 | good |
| | 6 | 0.3 | good |
| | 7 | 0.5 | good |
| | 8 | 0.2 | good |
| | 9 | 0.2 | good |
| | 10 | 0.3 | good |
| Comparative Example | 1 | 0.1 | good |
| | 2 | 2.4 | marginal |
| | 3 | 1.1 | marginal |
| | 4 | 4.1 | NG |

TABLE 8

| | | Odor (level indication value) | | | | |
|---|---|---|---|---|---|---|
| | | Before treatment | After cleaning | After treatment | 4 weeks after treatment | 10 weeks after treatment |
| Working Example 1 | Sink | 484 | 379 | 34 | 20 | 25 |
| | Urinal shelf | 547 | 339 | 106 | 17 | 33 |
| | Toilet stall | 448 | 322 | 95 | 43 | 45 |
| Comparative Example 1 | Sink | 445 | 317 | 68 | 98 | 135 |
| | Urinal shelf | 504 | 298 | 104 | 135 | 174 |
| | Toilet stall | 467 | 334 | 92 | 129 | 171 |

TABLE 9

| | | Number of red colonies | | | | |
|---|---|---|---|---|---|---|
| | | Before treatment | After cleaning | After treatment | 4 weeks after treatment | 10 weeks after treatment |
| Working Example 1 | Sink | 206 | 123 | 5 | 1 | 1 |
| | Urinal wall | 130 | 55 | 0 | 0 | 0 |
| | Urinal floor | 144 | 38 | 3 | 27 | 9 |
| | Toilet stall wall | 88 | 12 | 1 | 0 | 0 |
| | Toilet stall floor | 105 | 95 | 9 | 32 | 28 |
| Comparative Example 1 | Sine | 185 | 84 | 82 | 102 | 124 |
| | Urinal wall | 146 | 65 | 63 | 74 | 88 |
| | Urinal floor | 185 | 40 | 51 | 56 | 75 |
| | Toilet stall wall | 105 | 36 | 31 | 51 | 42 |
| | Toilet stall floor | 110 | 61 | 52 | 49 | 54 |

Japanese Patent Application No. 2017-190160 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A deodorizing/antibacterial/antifungal agent comprising a mixture of the following two kinds of fine particles dispersed in an aqueous dispersion medium:
   (i) titanium oxide fine particles, and
   (ii) alloy fine particles containing an antibacterial/antifungal metal and a metal constituent selected from the group consisting of silver-copper, silver-palladium, silver-platinum, silver-tin, gold-copper, silver-nickel, silver-antimony, silver-copper-tin, gold-copper-tin, silver-nickel-tin, silver-antimony-tin, platinum-manganese, silver-titanium, copper-tin, cobalt-copper, zinc-magnesium, silver-zinc, copper-zinc, silver-copper-zinc and combinations thereof,
   wherein the mixture of titanium oxide fine particles (i) and antibacterial/antifungal metal-containing alloy fine particles (ii) has a volume-based 50% cumulative distribution size ($D_{50}$), as measured by dynamic laser light scattering, of from 5 to 100 nm, and the mixing proportion of the titanium oxide fine particles and the alloy fine-particles, expressed as the weight ratio of titanium oxide fine particles/alloy fine particles, is between 100 and 100,000.

2. The agent of claim 1, wherein the antibacterial/antifungal metal contained in the alloy fine particles (ii) is at least one metal selected from the group consisting of silver, copper and zinc.

3. The agent of claim 2, wherein the antibacterial/antifungal metal contained in the alloy fine particles (ii) includes at least silver.

4. The agent of claim 1, wherein the amount of antibacterial/antifungal metal contained in the alloy fine particles (ii) is from 1 to 100 wt % based on the total weight of the alloy fine particles.

5. The agent of claim 1, further comprising a binder.

6. The agent of claim 5, wherein the binder is a silicon compound-based binder.

7. A member having the deodorizing/antibacterial/antifungal agent of claim 1 on a surface thereof.

8. The agent of claim 1, wherein the alloy fine particles (ii) comprise an alloy containing at least two antibacterial/antifungal metals.

9. The agent of claim 1, wherein the alloy fine particles (ii) comprise an alloy containing at least one antibacterial/antifungal metal and at least one metal other than a metal that increases antibacterial/antifungal properties.

10. The agent of claim 1, wherein the mixing proportion of the titanium oxide fine particles and the alloy fine-particles, expressed as the weight ratio of titanium oxide fine particles/alloy fine particles, is between 100 and 5,000.

* * * * *